United States Patent [19]

Brown, Jr.

[11] 4,289,891

[45] Sep. 15, 1981

[54] SILICONE DIFFUSION PUMP FLUIDS

[75] Inventor: Edgar D. Brown, Jr., Schenectady, N.Y.

[73] Assignee: General Electric Company, Waterford, N.Y.

[21] Appl. No.: 898,747

[22] Filed: Apr. 21, 1978

[51] Int. Cl.$^3$ .............................. C07F 7/08
[52] U.S. Cl. .................... 556/453; 556/455; 252/78.3
[58] Field of Search ............... 260/448.2 R; 556/453, 556/455

[56] References Cited

U.S. PATENT DOCUMENTS

| | | | |
|---|---|---|---|
| 2,410,346 | 10/1946 | Hyde | 556/453 X |
| 2,530,356 | 11/1950 | Hunter | 556/453 X |
| 2,611,774 | 9/1952 | Tyler | 556/453 |
| 2,890,234 | 6/1959 | Fletcher et al. | 556/453 |
| 3,012,052 | 12/1961 | Simmler | 556/455 |
| 3,389,159 | 6/1968 | Nielsen | 556/455 |
| 3,523,131 | 8/1970 | Sliwinski | 556/453 |
| 4,113,760 | 9/1978 | Frey et al. | 556/455 X |

FOREIGN PATENT DOCUMENTS

| | | | |
|---|---|---|---|
| 560981 | 7/1958 | Canada | 556/453 |
| 1205969 | 12/1965 | Fed. Rep. of Germany | 556/453 |
| 586187 | 3/1947 | United Kingdom | 556/455 |
| 848719 | 9/1960 | United Kingdom | 556/455 |
| 215993 | 11/1968 | U.S.S.R. | 556/453 |

OTHER PUBLICATIONS

Noll, "Chemistry & Technology of Silicones", 2nd ed., Academic Press, N.Y. (1968), pp. 461-463 and 630.
Noll, "Chemistry and Technology of Silicones", 2nd ed., Academic Press, N.Y. (1968), pp. 190-198.

*Primary Examiner*—Paul F. Shaver
*Attorney, Agent, or Firm*—Michael J. Doyle; John L. Young; Philip L. Schlamp

[57] ABSTRACT

The present invention relates to a variety of silicone diffusion pump fluids which are inexpensive to produce. An example of a preferred diffusion pump fluid of the present case is one of the formula,

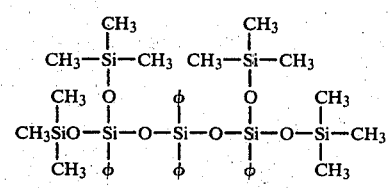

where $\phi$ is phenyl and such that the fluid boils at 245° C. at 1.5 mm. of Hg pressure. The present invention also has within its scope a process for producing such silicone diffusion pump fluids by hydrolyzing the appropriate chlorosilanes by a reverse hydrolysis procedure, that is, adding the appropriate amount of water to the mixture of chlorosilanes.

12 Claims, No Drawings

SILICONE DIFFUSION PUMP FLUIDS

BACKGROUND OF THE INVENTION

The present invention relates to silicone diffusion pump fluids and more particularly the present invention relates to silicone diffusion pump fluids which are relatively inexpensive to produce as compared to other silicone diffusion pump fluids.

Diffusion pumps are well known. Such pumps are connected to mechanical vacuum pumps and are used to produce vacuums in $1 \times 10^{-4}$ to the $1 \times 10^{-8}$ millimeters of Hg pressure at 25° C. Such apparatuses are utilized to form vacuums in many manufacturing operations as well as in many testing facilities. For instance, such diffusion pumps are utilized to form space chambers for the testing of apparatus and equipment that are to be utilized in space operations. In addition, such diffusion pumps are utilized to produce vacuums for the removal of gases from steel in the process of making certain types of steel. Further, it is well known that such diffusion pumps are utilized to produce vacuums so as to facilitate the depositing of thin metallic films on plastics, glass and other substrates. For instance, a diffusion pump is utilized to produce the necessary vacuum for the deposition of thin metallic coating on the internal face of television tubes.

Accordingly, diffusion pumps have a wide use in industry, as well as in laboratories for the testing and production of various articles. The way a diffusion pump works is that it contains a diffusion pump fluid in a chamber which diffusion pump fluid is heated at a constant rate. The diffusion pump fluid is vaporized and the vapor is forced through a jet in the center of an outer chamber containing the gas molecules to be removed. As it leaves the jet the vaporized fluid is forced downward by deflection member against the walls of the outer chamber which are cooled. As a result the vaporized fluid condenses entraining with it as it condenses the gas molecules to be removed. Then the condensed fluid returns to the boiling chamber of the diffusion pump. The gas is driven off by heating and sent to the mechanical pump where it is exhausted. The cooled and degassed diffusion pump fluid is then recirculated to the heated diffusion pump chamber where it is once more used to entrain gases.

It can be appreciated that diffusion pump fluid must have certain necessary properties. Thus, it must be a fluid which has the proper boiling range and will not give off vapors or gases of its own. It is also a fluid which will boil without bumping, that is, it will boil smoothly and has a steep vapor pressure curve. The diffusion pump fluid is also one that desirably can absorb a lot of gas when it is hot and has a very low absorbance of gases at room temperature.

It has been said by the diffusion pump industry that the right boiling temperatures for the fluid in a diffusion pump should be in the neighborhood of 200° to 225° C. at 1-2 millimeters of mercury pressure. The heating rate of the diffusion pump fluid and the diffusion pump is also set at a fixed rate so as to comply with industry standards.

It would be desirable to be able to change diffusion pump fluid in a particular diffusion pump as the vacuum became better, that is, to insert at that point a diffusion pump fluid which would have the capacity to adsorb a further amount of the light gases, but in practice this is not possible. The industry practice has been to utilize one diffusion pump fluid per diffusion pump. Standardization of diffusion pump fluids and diffusion pumps and interchangeability thereof makes it easier for the use of such diffusion pumps in the industry and especially in the standardization of different processes in industry, for instance, in standardization of the process for depositing of the metallic film on the interface of television picture tubes.

As can be appreciated in the operation of a diffusion pump, the diffusion pump fluid is a critical part in the operation of the pump. Accordingly, much time and effort has been expended in the development and selection of the proper types of diffusion pump fluids for diffusion pumps. There have been developed organic fluids for use as diffusion pump fluids. Examples of these are organic esters, chlorinated hydrocarbons, polynuclear aromatics and others. It should be noted that the silicone diffusion pump fluids have an advantage over the organic diesters in that they are more stable at elevated temperatures. The chlorinated hydrocarbons are not desired because of toxicity problems. In addition, the polynuclear aromatics, organic diffusion pump fluids, as well as the polyphenylethers are very expensive and difficult to produce, thus, commanding a very high price in the market. Accordingly, silicone diffusion pump fluids have been developed in the past. It should be noted while such silicone diffusion pump fluids had several advantages in that they were not as toxic as some of the organic materials and were more stable at high temperatures, nevertheless, most of such silicone fluids have turned out to be very expensive. Examples of silicone diffusion pump fluids sold and manufactured by Dow Corning Corporation, Midland, Mich. are as follows: DC-700 which is essentially a light end material. Along with this material there was a comparable material, DC-702, which is a mixture of methyl and methylphenyl cyclicpolysiloxanes. While DC-702, for instance, was utilized in steel mills and was more effective in creating a vacuum than the organic diesters, nevertheless, it has been found by experience that good diffusion pump fluids are produced from a single polymer specie. When the diffusion pump fluid is composed of a mixture of polymer species, such as in DC-700 and DC-702, then the diffusion pump fluid is not very effective or is not as effective as desired because the composition has a low boiling point. In the formulas below, $\phi$ stands for phenyl.

Accordingly, other diffusion pump fluids that were developed by Dow Corning Corporation were DC-704 of the formula,

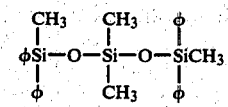

and DC-705 having the formula,

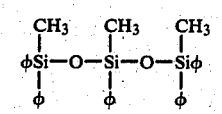

While DC-704 is acceptable and better than DC-702 or DC-700 in its characteristics as a diffusion pump fluid, and the best diffusion pump fluid manufactured and sold by Dow Corning Corporation is DC-705 which is capable of producing a vacuum of up to $1\times 10^{-8}$ millimeters of Hg pressure, however, such diffusion pump fluids such as DC-704 and DC-705 were very expensive to produce because of the esoteric chain-stoppers or terminal siloxy units in the polymer chain that were used to produce the polymer. These esoteric chain-stoppers to some silicone manufacturers were not ones that were obtained as byproducts from normal silicone processes in a silicone manufacturing plant and had to be specially produced. Accordingly, there resulted a high cost for the production of such silicone polymers. As a result, while such silicone polymers were excellent diffusion pump fluids, nevertheless, they were very expensive to produce and commanded a high price at the market place.

Accordingly, it was highly desirable to produce a cheap diffusion pump fluid. One attempt at this was the production of a polymer having the formula,

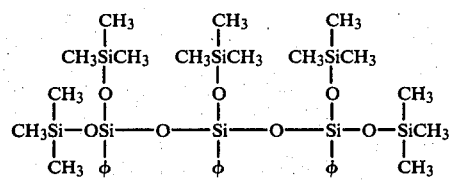

where $\phi$ stands for phenyl. While having about the same diffusion pump characteristics as DC-702 in terms of creating a vacuum, nevertheless, the above compound was expensive to produce because it was obtained in very low yields by the processes normally used to prepare it. Attempts were made to reduce the cost of the production of such fluids. However, even after repeated attempts at improving the yield of the desired product there only resulted a 30% yield of the desired product. In addition, the product contained trifunctional siloxy cyclicpolysiloxanes which would evaporate from the rest of the fluid when the fluid was used as diffusion pump fluid in a diffusion pump and create problems in its performance. In the course of such research, there was developed a diffusion pump fluid which had good boiling point characteristics. This fluid had the structure,

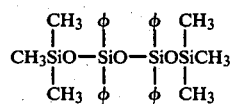

where $\phi$ stands for phenyl. The difficulty with such diffusion pump fluid while it had good boiling characteristics and good vapor pressure characteristics and it was cheap to produce was that it had a melting point at 46° C. and any normal modifications in the formulations only changed the melting point slightly. Accordingly, in normal operations of a diffusion pump such a diffusion pump fluid would solidify at room temperature and cause problems in handling in the diffusion pump.

Accordingly, it was highly desirable to develop inexpensive silicone diffusion pump fluid which could be made by a simple process utilizing as reactants chlorosilanes normally found or normally produced in a silicone manufacturing plant. It was also desirable to produce inexpensive diffusion pump fluids which could effectively compete with diffusion pump fluids, DC-704 and DC-705, produced by Dow Corning Corporation.

Accordingly, it is one object of the present invention to produce an inexpensive diffusion pump fluid by a simple process which could be utilized as an offset to existing diffusion pump fluids.

It is an additional object of the present invention to provide an efficient process for producing an inexpensive diffusion pump fluid.

It is still an additional object of the present invention to provide for a reverse hydrolysis procedure for producing an inexpensive diffusion pump fluid.

It is yet an additional object of the present invention to provide for a simple process for producing inexpensive silicone diffusion pump fluids which will perform almost as effectively or as effectively as the more expensive diffusion pump silicone fluids.

These and other objects of the present invention are accomplished by means of the disclosure set forth hereinbelow.

SUMMARY OF THE INVENTION

In accordance with the above objects there is provided by the present invention, a process for forming an inexpensive silicone diffusion pump fluid capable of reaching a vacuum of $1\times 10^{-6}$ in a vacuum pump comprising (1) reacting in sufficient amounts an aliphatic alcohol with phenyltrichlorosilane so as to substitute on the average from 40 to 80% of the chlorine groups in said silane with alkoxy groups so as to produce an alkoxylated phenylchlorosilane; (2) adding at least the stoichiometric amount of water to a mixture of said alkoxylated phenylchlorosilane, trimethylchlorosilane and a phenyl compound selected from the class consisting of diphenyldichlorosilane and diphenylsilane diol to form a mixture of diffusion pump fluids which are phenyl siloxane fluids, and (3) separating out the desired diffusion pump fluids by fractional distillation.

In accordance with the above process there were produced three desirable diffusion pump fluids, one of which is diffusion pump fluid of the formula,

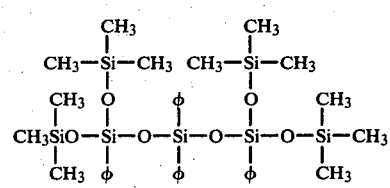

where $\phi$ is phenyl such that the fluid boils at 245° C. at 1.5 millimeters Hg pressure. There is also produced by the above process, which is a reverse hydrolysis process, a diffusion pump fluid of the formula,

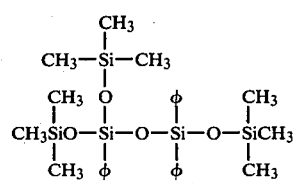

where $\phi$ is phenyl such that the fluid boils at 185° to 195° C. at 1.5 millimeters Hg pressure.

Finally, as another preferred diffusion pump fluid, there is produced by the above process, a diffusion pump fluid of the formula,

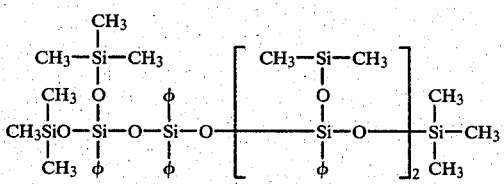

where φ is phenyl such that the fluid boils at a temperature in the range of 245° to 265° C. at 1.5 millimeters of Hg pressure.

It should be noted that of the above diffusion pump fluids, that the first diffusion pump fluid and the third diffusion pump fluid are the most preferred with the first of the diffusion pump fluids being the most preferred of all of the three of the fluids. However, all of the diffusion pump fluids whose formulas are given above can be produced by the above process and they can be utilized in diffusion pumps to produce a vacuum as low as $1 \times 10^{-6}$ millimeters of Hg pressure in the appropriate diffusion pumps.

DESCRIPTION OF THE PREFERRED EMBODIMENT

There are many ways to produce some quantities of the preferred diffusion pump fluids of the instant case. However, the difficulty with other than the preferred process for producing the preferred silicone diffusion pump fluids of the instant case is that the process will not operate efficiently or will not operate at all. Accordingly, if the appropriate chlorosilanes are added to water to hydrolyze and to produce the preferred diffusion pump fluids of the instant case, there often results a gel making the reaction products useless as diffusion pump fluids. Such a gel phenomena occurs even if hydrocarbon solvent is utilized to dissolve the chlorosilanes or the water. Accordingly, even in the case of a particular cosolvent for both water and the chlorosilanes such as, acetone, when the appropriate chlorosilanes are added to either the water or acetone or added to the acetone water mixture there usually results a gel or there results a variety of products most of which are useless. The preferred products are produced in very minor yields. Accordingly, it was altogether unexpected that an alkoxylation procedure as will be disclosed below in combination with the reverse hydrolysis procedure, that is, the addition of water to the chlorosilanes, would result in the desired products of the instant case.

In accordance with the process of the instant case there is first carried out an alkoxylation of the phenyltrifunctional silane that is utilized as a reactant in the process. The phenyltrichlorosilane is first alkoxylated with an aliphatic hydrocarbon alcohol and more preferably with an aliphatic alcohol having 1 to 3 carbon atoms such as, for instance, methanol, ethanol and propanol. It has been found that ethanol is the preferred alkoxylation alcohol in the process of the instant case since it is non-toxic.

Accordingly, the desired quantity of phenyltrichlorosilane is taken and there is added to it the desired amount of ethanol alcohol or any aliphatic alcohol having from 1 to 3 carbon atoms such that on an average at least one and more preferably at least two of the chloro groups in the silane is substituted by an alkoxy group. Accordingly, generally, the alcohol is reacted with the phenyltrichlorosilane such that on the average of 30-80% of the chlorine groups in the silane are substituted by alkoxy groups. More preferably, sufficient quantities of the aliphatic alcohol are reacted with a phenyltrichlorosilane such that from 60 to 70% of the chlorine groups are substituted by alkoxy groups. Most preferably, of course, two of the chlorine groups in the silane are substituted by alkoxy groups so as to yield phenyldialkoxychlorosilane. Accordingly, in the most preferred embodiment 66% of the chlorine groups in the phenyltrichlorosilane are substituted by alkoxy groups and most preferably by ethoxy groups. The reason for doing this is to yield a stable intermediate for utilization in the subsequent hydrolysis step.

It has been found that when phenyltrichlorosilane is hydrolyzed with the other chlorosilane reactants to produce the desired diffusion pump fluids of the instant case, that the phenyltrichlorosilane in such reaction is too reactive and produces many undesirable by-products which are not useful as diffusion pump fluids. Accordingly, in prior art processes where phenyltrichlorosilane was directly reacted with the other chlorosilanes such as, diphenyldichlorosilane and trimethylchlorosilane, the resulting diffusion pump silicone fluids were not obtained in very high yields and were obtained in only very minor yields with most of the products being undesirable phenyl cyclics and other materials which were not useful as diffusion pump fluids.

In the reaction of the aliphatic alcohol with the phenyltrichlorosilane preferably the alcohol is added to the phenyltrichlorosilane over a period of time with continuous agitation. Such addition of the aliphatic alcohol to the phenyltrichlorosilane may take place over a period of time of anywhere from 2 to 4 hours. After the four hour period in which the desired dialkoxyphenylchlorosilane is produced, then the mixture may be heated at a temperature of anywhere from 25° to 50° C. to remove excess alcohol and to remove hydrogen chloride that has been formed during the process. It can be understood, of course, if heating is carried out at a temperature of 25° to 50° C. then the heating of the mixture takes place under vacuum so as to remove the unreacted alcohol and the hydrogen chloride by-product. It is desirable to remove as much of the acid that has been formed during the alkoxylation process since such acid in the second step of the process would result in initiating and perpetuating the second reaction at a much faster rate than is desirable in the process of the instant case. If the second reaction in the process of the instant case is carried out at too rapid a rate, then there is a problem that undesirable by-products may be formed which are useless as diffusion pump fluids. Accordingly, it is desirable to treat the dialkoxychlorosilane such that its acidity is below 100 parts per million. After this has been done then the dialkoxyphenylchlorosilane is taken and there is mixed into it the appropriate amounts of diphenyldichlorosilane and trimethylchlorosilane. For the most preferred silicone diffusion pump fluid it is desirable to mix in the reaction pot at least two moles of the alkoxylated phenyl chlorosilane with at least 4 moles of the trimethylchlorosilane with one mole of diphenyldichlorosilane. Although other molar quantities can be utilized of these reactants it is preferred that of the above at least 4 moles of trimethylchlorosilane with at least 2 moles of the dialkoxyphenylchlorosilane be present per mole of the diphenyldichlorosilane since this produces the largest quantities of the desired product. If other than the above moles of the quantities of reactants are utilized then the desired products will be produced but at much lower yields as can be expected. This would result from the fact that the appropriate molar quantities of the reactants were not present to preferentially produce a silicone diffusion pump fluid having four trimethylsiloxy groups, two phenyltrifunctional siloxy groups and one diphenyldifunctional siloxy group. It also should be noted that either diphenyldichlorosilane may be utilized as a reactant or diphenylsilane diol. It has been found that the reaction proceeds much more readily with diphenyldichlorosilane rather than with the diol.

Accordingly, after the ingredients are put into the reaction pot, there is added to them water to hydrolyze the chlorosilanes and produce the desired silicone diffusion pump fluid. In the preferred embodiment of the instant case, there must be utilized at least the stoichiometric amount of water necessary to hydrolyze all the chlorine groups in the silanes. As can be appreciated, if less than the stoichiometric amount of water is present then there will not be sufficient water to hydrolyze off the chlorine groups and the desired diffusion pump fluids will be formed in a very small yield. On the other hand, it is desirable that not too much water be present. In the preferred embodiment of the instant case, at least 10% excess water over the stoichiometric amount needed to completely hydrolyze the chlorine groups is utilized in the reaction mixture. If less than 10% excess of water is utilized over the stoichiometric amount needed to hydrolyze the chlorine groups, then the desired silicone diffusion pump fluids are produced. However, such silicone diffusion pump fluids are not produced in very high yields and there results an undesirable amount of useless by-products. It should also be pointed out that if water is utilized considerably in excess of the 10% noted above, then such excess water serves no useful purpose.

It should be noted that such excess water has one disadvantage in that it will dissolve any hydrogen chloride that is formed during the hydrolysis process and thus making such acid hard to remove from the silicone diffusion pump fluid. It is desirable that such hydrogen chloride that is formed during the hydrolysis be removed from the final product since such acid will if allowed to remain in the final product cause some reversion of the fluid during storage. Accordingly, for these reasons, it is desirable that the acid content of the final silicone diffusion pump fluid not exceed 100 parts per million and more preferably not exceed 15 parts per million. It should be noted that in this process the water must be added to the chlorosilanes, not the chlorosilanes added to the water. This is the reverse hydrolysis procedure. If the chlorosilanes are added to the water as is normal in hydrolysis of chlorosilanes, then what most likely will take place is that the silanes will gel. It is also desirable that the water not be added to the chlorosilanes in a single addition, but that the water be added continuously in small increments to the chlorosilanes over a period of time. It is also desirable that during the addition of water to the chlorosilanes that the chlorosilanes be agitated vigorously and continuously during the entire hydrolysis process.

Accordingly, with vigorous agitation of the chlorosilane mixture, the water is added continuously over a period of time varying from 2 to 4 hours or more until the water has been completely added to the agitated chlorosilanes. It should be noted that the reaction period for the addition of the water to the chlorosilanes, as well as the total reaction time for the reaction may vary anywhere from 4 to 6 hours. It is preferred that after all the water has been added to the chlorosilanes that the chlorosilanes be continuously agitated and allowed to equilibrate and react with the water for an additional period of time of 1 to 2 hours such that the total reaction time may vary anywhere from 2 to 6 hours or more. The most preferable reaction time for the addition of the chlorosilanes to the water is desirably of long duration since a shorter reaction time does not permit as predictable a reaction of the chlorosilanes with the water to produce the desired silicone diffusion pump fluids and in addition a shorter reaction time does not allow the reaction mixture to fully equilibrate to produce the maximum amount of the desired silicone product. Accordingly, the reaction time for the production of the diffusion pump fluids in the hydrolysis reaction is desirably 4 or 6 or more hours allowing for equilibration of the silicone products that are formed so as to yield a minimum of undesirable by-products.

It should be noted that no solvent is used in this hydrolysis reaction. It has been found that when a solvent is utilized even with a reverse hydrolysis procedure as compared to the straight hydrolysis procedure, that the solvent performs no useful function and in addition increases the formation of undesirable by-products in high yields. Accordingly, it has been found that even polar hydrocarbon solvent such as acetone, promotes the formation of undesirable by-products in high yields when it is utilized as a solvent in the instant process. This is even though the acetone in large quantities will solvate the chlorosilanes and the water producing a homogeneous hydrolysis medium.

Another necessary aspect to the present reaction process is the reaction temperature in which the hydrolysis reaction takes place. Generally, the hydrolysis reaction can take place at a reaction temperature of anywhere from −8 degrees centigrade to 25° C. However, it has been noted that more of the desired silicone diffusion pump fluids are produced when the temperature is as low as possible. It should be noted that the reaction is endothermic, that is, by the addition of the water to the chlorosilanes heat is absorbed by the reactants such that the temperature of the reactants decrease to a range of 0° C. or below. However, it is preferred to utilize refrigeration such that the temperature during the entire process or during the entire addition of the water to the chlorosilanes is maintained in the neighborhood of 0° C. and more preferably maintained in the range of 5 to −8° C.

Accordingly, after the reaction procedure as outlined above has been followed and the reaction temperature has been maintained in the range of anywhere from −8 to 25° C., and more preferably from −8 to 5° C., there is produced the preferred diffusion pump fluids of the instant case in high yield. At that time it is only necessary to reduce the acidity of the reaction mixture by removing the hydrogen chloride that has formed and to remove excess water and excess alcohol. It should be noted that the water and HCl may be removed by stripping from the mixture by heating the reaction products at a temperature from anywhere from 50° to 100° C. under vacuum. The hydrogen chloride content of the reaction product may also be diminished to the appropriate level by washing the reaction product with water. Since the water is insoluble in the silicone reaction products, it may be simply removed by decantation. It should be noted that this procedure will remove the minor amounts of hydrogen chloride and alcohol that is present in the silicone reaction products after the hydrolysis reaction has been completed. In a preferred process to remove alkoxies from the products and reduce the silanol content, there may be added to the product an acid activated clay such as Filtrol manufactured by Filtrol Corporation of Los Angeles and trimethylchlorosilane and the resulting mixture is heated above 100° C. to replace the alkoxies and silanol and remove the water and alcohol. After reaction is complete and most of the alcohol and water is removed, then the Filtrol may be removed by filtering to yield the product. It should also be noted that if the preferred process as outlined above is carried out, that is, that the water not be considerably in excess of 10% of the stoichiometric amount, then the excess hydrogen chloride that is formed during the process will not become dissolved in the excess water. Since the hydrogen chloride is insoluble in the siloxane products, it will leave the mixture and will not be retained in the siloxane mixture unless there is considerable excess water present. Accordingly, in the less preferred embodiment the foregoing stripping procedure as well as the washing with water is solely for the purpose of removing these minor amounts of acid that may still be retained in the siloxane hydrolysis product mixture. It should be noted that the stripping procedure is not preferred in removing the hydrogen chloride that is formed in the process since in the presence of an acid and upon heating the mixture, the desired yield of a desired siloxane diffusion pump fluid may be reduced.

Accordingly, in another embodiment the siloxane product mixture is simply washed with water a number of times until the acid content has been reduced to the appropriate level. If necessary, a mild base may be added to the siloxane products so as to neutralize any additional acid that is present so that the final acid content of the siloxane diffusion pump product does not exceed 100 parts per million and preferably does not exceed 15 parts per million. It should be noted that the acid content of the diffusion silicone pump fluid should be as low as possible, otherwise, at those high temperatures at which the diffusion pump fluid is used if the acid content is too high then the acid would cause reversion of the siloxane fluid to undesirable siloxane by-products.

It should also be noted that an example of a mild base which can be utilized in the final neutralization of the acid in the siloxane diffusion pump fluids is in one instance sodium bicarbonate. Other mild bases can also be used. After the acid has been neutralized in the siloxane reaction products and the excess water removed from the reaction product, then it is only necessary to fractionally distill the siloxane products to obtain in substantially pure quantities the different fractions. Accordingly, by such fractional distillation, there is obtained as products, first, a fraction that boils at the range of temperatures of 175° to 185° C., which fraction is basically a mixture of phenyltrifunctional siloxy cyclicpolysiloxanes which are not useful as diffusion pump fluids. Such a material is normally obtained in a yield of 10 to 15%.

There is also obtained a fraction which boils at 245° C. at 1.5 millimeters of Hg pressure which has the formula,

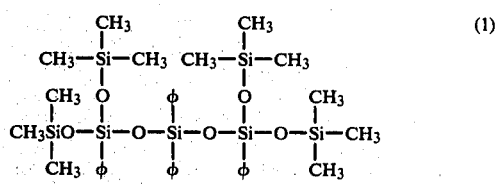

where $\phi$ is phenyl. The above phenyl siloxane is the most preferred diffusion pump fluid of the instant invention and is normally obtained in accordance with the preferred process of the instant case at a yield of 40 to 60%.

There is also obtained by fractionally distilling the siloxane products of the process of the instant case, a fraction that boils at 185° to 195° C. at 1.5 millimeters of Hg pressure which is siloxane diffusion pump fluid identified as having the formula,

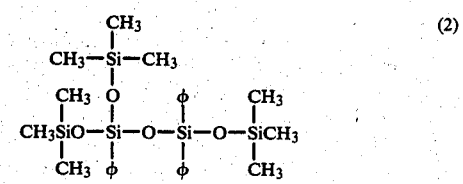

where $\phi$ is phenyl. The above phenyl siloxane of Formula (2) is a less preferred diffusion pump fluid since it is not as high boiling as the other fluid that was mentioned previously. It can, nevertheless, be utilized in diffusion pump fluids where it is not desired to produce as high a vacuum and is obtained at a yield of 20 to 30%.

Finally, there is obtained by fractional distillation siloxane reaction products of the above process, a fraction which can be used as a silicone diffusion pump fluid and which has been identified to be a siloxane of the formula,

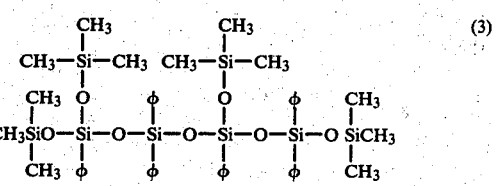

where $\phi$ is phenyl and such that the above fluid of Formula (3) boils at a temperature of 245°–265° C. at 1.5 millimeters of Hg pressure. Such phenylsiloxane which is one of the preferred diffusion pump fluids of the instant case is obtained at a yield of 5 to 10% by the above reverse hydrolysis process. It should be noted that the above reverse hydrolysis process of the instant case produces the foregoing diffusion pump fluids of Formulas (1), (2) and (3) at relatively high yields, while utilizing as ingredients and intermediate compounds which are normally available in a silicone manufacturing plant.

It should be noted that as mentioned previously all of the intermediates and starting products for producing the foregoing silicone diffusion pump fluids are normally available in a silicone plant and do not have to be especially manufactured for the specific purpose of producing the foregoing silicone diffusion pump fluids. As a result, because of the high yields obtained in the instant process and because of the availability of the starting materials, the diffusion pump fluids of the preferred process of the instant case can be produced efficiently and economically compared to the prior art silicone diffusion pump fluids. It should be noted that as far as the performance in the diffusion pump, the silicone diffusion pump fluid of Formula (1) compares very favorably with DC-704 which was identified previously, and that the silicone diffusion pump fluid of the instant process of Formulas (2) and (3) compare very favorably in performance with the DC-702 product which was discussed previously.

In accordance with the instant invention there is also intended to be disclosed as within the ambient of the instant invention other silicone diffusion pump fluids which can be produced by the reverse hydrolysis procedure or by a straight hydrolysis procedure, but which silicone diffusion pump fluids are more expensive to produce because of the necessity of utilizing silane intermediates which are not readily available. However, it is believed that these less preferred embodiments of silicone diffusion pump fluids are important in the silicone diffusion pump fluid technology since they perform very capably as silicone diffusion pump fluids. Thus, these less preferred silicone diffusion pump fluids that will be disclosed below are preferred as silicone diffusion pump fluids since they are capable of producing high vacuums, that is, vacuums as good as $1 \times 10^{-8}$. Such less preferred silicone diffusion pump fluids, accordingly, compare very well in performance in diffusion pumps as compared to the foregoing DC-704 and DC-705 products. Accordingly, another silicone diffusion pump fluid within the scope of the instant invention, is one of the formula,

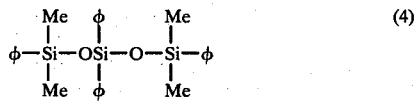

where Me stands for methyl and $\phi$ stands for phenyl.

Such a silicone diffusion pump fluid generally comprises hydrolyzing a mixture of at least 2 moles of phenyldimethylchlorosilane per mole of diphenyldichlorosilane and adding at least the stoichiometric amount of water to said mixture necessary to hydrolyze all the chlorine moieties in said silane. Although in this particular case the silicone diffusion pump fluid could be formed by adding the chlorosilanes to the water, a higher yield is obtained by the reverse hydrolysis of adding the water to the chlorosilane. Again, in this process it is preferred at least 10% in excess of stoichiometric amount of water be utilized in the process. In addition, it is desired that not too much excess water be utilized since that only dissolves the hydrogen chloride gas that is produced in the process and retains it in the product mixture. In addition, it is desirable that a solvent not be utilized in this hydrolysis procedure since such solvent such as, acetone only increases the amount of the undesirable by-products that are formed during the process. Again, the phenylsiloxane diffusion pump fluid that is formed from the process must be treated, that is, it must be washed and treated with a mild base if necessary, so that the acidity of the final product does not exceed 100 parts per million and more preferably does not exceed 15 parts per million. The same mild base as is utilized in the preferred process of the instant case may be used here.

It should be noted that this silicone diffusion pump fluid of Formula (4) is expensive to produce because of the expense of producing phenyldimethylchlorosilane. Such phenyldimethylchlorosilane is not normally produced in a silicone manufacturing plant and it has to be manufactured specially. Accordingly, for the above reasons the process for producing the diffusion pump fluid of Formula (4) is unduly expensive.

In addition, it should be noted that the yield of the desired silicone diffusion pump fluid of Formula (4), and in accordance with the above process is 70 to 80%, and such a silicone diffusion pump fluid of Formula (4) has a boiling point of 230° C. at 1.5 millimeters of Hg pressure.

Another less preferred silicone diffusion pump fluid in accordance with the instant invention is the fluid of the formula,

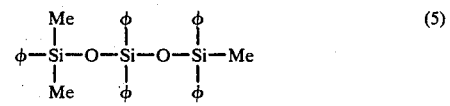

where $\phi$ stands for phenyl and Me is methyl. Such silicone diffusion pump fluid of Formula (5) above, as was the case with the silicone diffusion pump fluid of Formula (4), compares very favorably in performance with DC-704 and DC-705. However, the intermediates for producing such silicone diffusion pump fluid of Formula (5) are difficult to come by in a silicone manufacturing plant and usually have to be specially produced. Accordingly, for this reason the expense for producing such a silicone diffusion pump fluid of Formulas (4) and (5) is very high and considerably in excess of that needed to produce the silicone diffusion pump fluids of Formulas (1), (2) and (3). Silicone diffusion pump fluids of Formulas (1), (2) and (3) are produced from intermediates which are readily available in silicone manufacturing plants; that is, the diphenyldichlorosilane, the trimethylchlorosilane and the phenyltrichlorosilane are intermediates which are readily available in any silicone manufacturing plant. Accordingly, to produce the silicone diffusion pump fluid of Formula (5), the process generally comprises forming a mixture of at least one mole of monophenyldimethylchlorosilane and at least one mole of methyldiphenylchlorosilane per mole of diphenyldichlorosilane and adding to this chlorosilane mixture at least the stoichiometric amount of water necessary to hydrolyze all the chlorine moieties in said silanes. It should be noted again, that in this process as with the case of the diffusion pump fluid of Formula (4), that the hydrolysis procedure can be either a straight hydrolysis procedure or reverse hydrolysis procedure. Generally, the reverse hydrolysis procedure is preferred in which the water is added to the chlorosilane mixture, since the amount of undesirable by-products is reduced by such a reversed hydrolysis procedure. In addition, preferably, there is utilized at least 10% excess water above the stoichiometric amount necessary to completely hydrolyze all the chlorine moieties in the chlorosilanes. The 10% excess water allows the proper hydrolysis to form a maximum amount of the diffusion pump fluid of Formula (5), with the minimum amount of undesirable by-products. In addition, excess water of more than 10% of the excess amount is not desired since the excess water serves no useful purpose.

In addition, again it is desirable that no hydrocarbon solvent be utilized in the hydrolysis reaction. The use of a solvent only decreases the amount of the desired yield of the desired product. It should also be noted that both in the process of producing the diffusion pump fluid of Formulas (4) and (5) that the reaction temperature may generally vary anywhere from −8° to 25° C. and more preferably varies in the range of −8° to 5° C.

In addition, in both processes it is preferred that the water be added intermittently to the chlorosilanes during a period of time varying anywhere from 2 to 4 hours and that the total reaction time for the production of the diffusion pump fluid of Formulas (4) and (5) take place over a period of time varying anywhere from 4 to 6 hours or more.

It is desirable that the reaction time of the hydrolysis reaction for forming the silicone diffusion pump fluid of Formulas (4) and (5) be in the time periods indicated above since if a shorter reaction time is utilized then sufficient intimate contact between the water and the chlorosilanes is not obtained. Utilizing the above process, there is obtained the silicone diffusion pump fluid of Formula (5) above in generally a yield of 30 to 40%. Such a silicone diffusion pump fluid of Formula (5) above has boiling point of 255° C. at 1.5 millimeters of Hg pressure.

Finally, a less preferred diffusion pump fluid in accordance with the instant invention is one of formula,

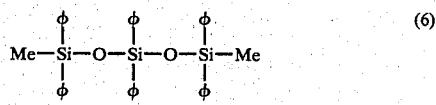

where φ is phenyl and Me is methyl. A process for forming a silicone diffusion pump fluid of Formula (6) above comprises forming a mixture of at least 2 moles of methyldiphenylchlorosilane per mole of diphenyldichlorosilane and adding to this chlorosilane mixture at least the stoichiometric amount of water necessary to completely hydrolyze all the chlorine moieties in said silanes. Again the reaction conditions in the process is much the same as producing the silicone diffusion pump fluids of Formulas (4) and (5).

It should be noted that again the reaction temperature for the hydrolysis reaction is preferably in the range of −8° to 25° C. and more preferably in the range of −8° to 5° C., and that the reaction period can vary anywhere from 4 to 6 hours. It is also desirable that the water be added incrementally to the chlorosilanes over a period of time of anywhere from 2 to 4 hours or more. Again, as stated previously, with the other less preferred diffusion pump fluids, although a straight hydrolysis procedure may be utilized to hydrolyze the foregoing chlorosilanes to produce the diffusion pump fluid of Formula (6), it is preferred that a reverse hydrolysis procedure be utilized in which the water is added to the chlorosilane mixture. It is also desirable in this process for producing the silicone diffusion pump fluid of Formula (6) that at least 10% excess water over the stoichiometric amount needed to completely hydrolyze the chlorosilane mixture be utilized. Also, in addition, in the production of all the less preferred diffusion pump fluids of Formulas (4), (5) and (6), it is preferred that the final silicone diffusion pump fluid not have an acid content that exceeds 100 parts per million and more preferably does exceed 15 parts per million since the acid will cause reversion or breakdown of the diffusion pump fluid to form undesirable by-products when the fluid is heated to high temperatures. Accordingly, after the silicone diffusion pump fluid has been formed then the acidity can be reduced by washing with water which is insoluble in the siloxane and further by the addition of a mild base to the siloxane diffusion pump fluid so that it does not have an acidity in excess of the limits set forth previously. Utilizing the above process there is obtained the silicone diffusion pump fluid of Formula (6) at a yield of generally 25 to 35% and which fluid has a boiling point of 260° C. at 1.5 millimeters of Hg pressure. It should be noted that in the foregoing processes for producing silicone diffusion pump fluids of Formulas (4), (5) and (6), a reversed hydrolysis procedure was recommended since that increases the yield of the desired product as compared to the process utilized in the straight hydrolysis, that is the addition of the chlorosilanes to water.

In addition, there could be utilized a process in which instead of diphenyldichlorosilane there is utilized diphenylsilane diol as a reactant. However, it has been found the process if carried out more rapidly and more efficiently with the use of the diphenylchlorosilane. However, the diphenylsilane diol could be utilized in the instant process with minor difference in yield. It should be noted that the diphenylsilane diol is formed from the diphenyldichlorosilane, thus adding an additional step to the above process. In addition, the silanols could be formed from all of the chlorosilane reactants in the process for forming the diffusion pump fluids of Formulas (4), (5) and (6) and then the silanols reacted in a condensation reaction in the presence of an acid to form the appropriate diffusion pump fluid of Formulas (4), (5) and (6). However, such a process involves additional steps in forming the silanols from the chlorosilanes and, thus, increases the cost of producing the diffusion pump fluids. It should be noted that the diffusion pump fluid of Formula (6), above, while simple to produce it is nevertheless, expensive since the methyldiphenylchlorosilane intermediate from which it is produced has to be made specially by most silicone manufacturers and is not readily available in silicone manufacturing plants. Accordingly, for the above reasons, the diffusion pump fluids of Formulas (1), (2) and (3) are preferred in the instant case. That is, while the silicone diffusion pump fluids of Formulas (4), (5) and (6) perform very favorably as diffusion pump fluids as compared to DC-704 and more particularly DC-705, which is an excellent diffusion pump fluid, nevertheless, the diffusion pump fluids of Formulas (1), (2) and (3) perform capably as compared to DC-704, a Dow Corning product, and are much less expensive to produce than the diffusion pump fluids of Formulas (4), (5) and (6).

In the data given in the Examples below the different diffusion pump fluids that were produced were tested in the G-4 diffusion test which is standard in the diffusion pump industry. Such a test comprises taking a glass diffusion pump which has been standardized, that is, it is a single stage pump which is connected to a deadhead with an ion gauge. To the pump chamber there is added 40 ml. of the diffusion pump fluid that is to be tested and there is applied to the diffusion pump a standard voltage of 46 volts to the heating element. A standard mechanical pump is used as a backing element to the diffusion pump. There is connected a Pirini gauge at the connecting link between the diffusion pump and the mechanical vacuum pump. The mechanical vacuum pump is one that is of ½ horsepower. The amount of excellence of the diffusion pump fluid is the vacuum that is formed as measured by the ion gauge in 4 hours of operation.

The Examples below are given for illustrating the present invention. They are not given for any purpose of setting limits and defining the scope of the instant invention. All parts in the Examples are by weight.

EXAMPLE 1

There was used 423 parts of phenyltrichlorosilane, 187 parts of ethanol, 253 parts of diphenyltrichlorosilane, 434 parts of trimethylchlorosilane and 100 parts of water. The phenyltrichlorosilane was placed in an agitated vessel and heated to 50-60° C. under a slight vacuum (200-300 mm/Hg). Ethanol was added slowly and the resulting HCl was exhausted and scrubbed. At the completion of the ethoxy addition, the reactants were held for 1 hour at 60° C. and the pressure was gradually decreased to the limit of the asperator (140 mm). At that time, the diphenyldichlorosilane and trimethylchlorosilane were added and mixed for ½ hour. Water was added, gradually keeping the pot temperature as near as possible to 5° C. Since this is an endothermic reaction this can be controlled by water addition rate. After total water addition, including 10% excess of the theoretical amount, the reactants were heated to 50° C. and held there for one hour to complete hydrolysis. The top layer consisting of ethanol, HCl and excess water was removed and the remaining product was washed with a Na₂SO₄ solution until neutral. Sodium bicarbonate can also be used here. The neutral oil was then fractionated to yield a 40 to 50% yield of a compound of the formula,

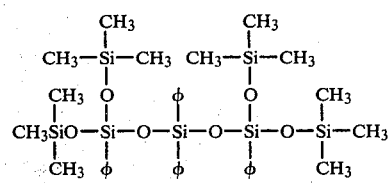

EXAMPLE 2

There was used as reactants 31 parts of phenyltrichlorosilane, 19 parts of diphenyldichlorosilane, 32 parts of trimethylchlorosilane, 5 parts of methanol, 8 parts of water and 5 parts of hexamethyldisiloxane. To a suitable kettle equipped to discharge HCl safely, there was added phenyltrichlorosilane. Under agitation, there was added methanol slowly. The reaction is endothermic but proceeds rapidly and without difficulty. Addition should take 30 minutes. If desired acid may be reduced by applying vacuum. This increases the speed of the next reaction but is not required. Then there was added the remaining silanes, diphenyltrichlorosilane and trimethylchlorosilane. It was agitated until well mixed, in 30 minutes. Then there was added Part I water, slowly. Addition should take between 1½ and 2 hours. The reaction is endothermic, slow to initiate and slow to complete. The ideal temperature was 10°-20° C. After all the water was added it was stirred for one hour. There was added a volume of water equal to the Part I water and heated gently. It was held at 40°-60° C. for one hour. At this time the phases were allowed to separate. This may be quite difficult. Also, there was added hexamethyldisiloxane to reduce density. There was drawn off and discarded the acid water layer. The silicone phase was washed with at least two applications. In the first wash there was used a 15% solution of sodium sulphate; in the second, a 15% solution of sodium bicarbonate and 10% sodium sulphate solution. Then it was heated to 80° C. and held for 2 hours. The results showed less than 250 ppm HCl. The product may either be dried by azeotroping (hexane and/or hexamethyldisiloxane as the organic phase) or dry by filtration after treatment with anhydrous sodium sulphate. If azeotroping is selected some dissolved salts, sodium bicarbonate and sodium sulphate will remain and the amount of Filtrol must be increased to compensate. If salt deposits are very heavy, it may be necessary to remove them. The mixture was heated to reflux or to 150° C. until all water and methanol was removed which required one hour. Then the dispersion was filtered to remove Filtrol #20. There is obtained at 42% yield a compound of the formula,

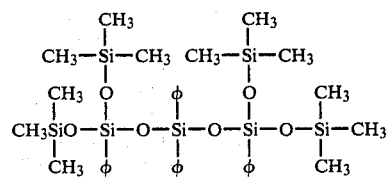

There is obtained at 24% yield a compound of the formula,

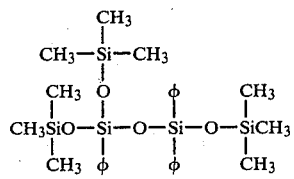

EXAMPLE 3

There is prepared a fluid of the formula,

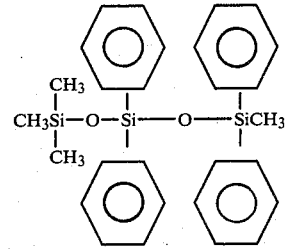

The physical properties of this fluid so far determined are:

| Viscosity | 0° F. | 31,200 |
|---|---|---|
| | 77° F. | 79 |
| | 100° F. | 39 |
| | 210° F. | 5.9 |
| Density 20° C. | | 1.063 |
| Density 100° C. | | 1.066 |
| Refractive Index | | 1.5555 |
| Boiling Point | | |
| 270 microns | | 200° C. |
| Coefficient of volumetric exposure | | $7 \times 10^{-4}$ |

There was used 22.3 parts of diphenylsilane diol, 10.2 parts of trimethylchlorosilane, 22.0 parts of diphenylmethylchlorosilane, 23.7 parts of pyridine (dried), and 21.8 parts of toluene. The diphenylsilane diol was dissolved in pyridine and one-half of the toluene was placed in an agitated vessel which was chilled. The chlorosilanes were dissolved in the remainder of the toluene and placed in an addition vessel. The silanes were added to the pyridine-silanoltoluene mixture at a rate which allowed the cooling system to keep the reaction between 5°-7° C. Careful control was not required, but for maximum yield temperatures did not exceed 10° C. In the laboratory, this addition required about 3 hours for a 5-liter batch. After all silanes have been added, the vessel was agitated for one hour and allowed to cool to room temperature. The pyridine salts were filtered and the solution was removed to a stripping vessel. The pyridine hydrochloride was then dissolved in an equal weight of water and the residual product solution was separated, dried with soda ash (2%) and added to that in the stripping vessel. The water solution of pyridine hydrochloride was retained for pyridine regeneration. The solution was stripped of toluene, pyridine, and pyridine hydrochloride. (20 mm. at 150° C. is sufficient). The critical part of diffusion pump manufacture was the purity that can be obtained. With this product and a relatively simple distillation, a purity which shows a single peak in V.P.C. measurements was obtained. For all practical purposes there was only three boilable components.

| | Boiling Point |
|---|---|
| $(CH_3)_3Si-O-\phi_2Si-O-Si(CH_3)_3$ | 108 at .5 mm |
| $(CH_3)_3Si-O-\underset{\underset{\phi}{\vert}}{\overset{\overset{\phi}{\vert}}{Si}}-O-Si\phi_2Me$ | 197 at .5 mm |
| $\phi_2CH_3Si-O-\underset{\underset{\phi}{\vert}}{\overset{\overset{\phi}{\vert}}{Si}}-O-Si\phi_2Me$ | 260 at .5 mm |

Distillation as the term is usually understood, is not possible with this product and a major portion of the process development contribution will be determination of proper equipment. The first fraction presents no difficulty, and any standard method can be used. During distillation of this fraction it was seen that no vapor was formed to condense in a distillation head. Instead, a wall of fluid gradually rises through the column and into the head. There was no take off until the wall of fluid reaches the take off. It was doubtful that much genuine fractionation either occurred or was needed. The temperatures generated at the head column and pot related more to the power input than to the boiling point of the fluid. As a further note, it was found to be impossible to redistill the product unless a higher boiling fraction is in the pot. In the laboratory, useable purity was obtained after less than 2% of the total charge had been removed at temperature. Following distillation, the forecuts were combined with the pot residue and placed in an equilibration kettle. (If there is doubt as to the dryness of the fractions, they should be filtered through a 50—50 mixture of soda ash and Fuller's earth). These were equilibrated with 0.35% dry KOH (This is a high KOH percentage but has given the best results) neutralized with 5% the weight of NaHCO$_3$ at 180° C. for 1 hour, filtered and distilled. This process was repeated as often as desired. Yield of the final product was 45% by weight.

EXAMPLE 4

There was produced a product of the formula,

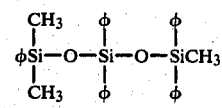

The physical properties of this fluid were

| Viscosity | 0° F. | Solid |
|---|---|---|
| | 77° F. | 181 |
| | 100° F. | 77 |
| | 210° F. | 9.1 |
| | Density 20° C. | 1.095 |
| | Density 100° C. | 1.039 |
| | Refractive Index | 1.5782 |
| | Boiling Point | |
| | 200 microns | 226° C. |

There was utilized 19.3 parts of diphenylsilane diol, 20.8 parts of diphenylmethylchlorosilane, 15.5 parts of dimethylphenylchlorosilane, 22.5 parts of pyridine (dried) and 21.9 parts of toluene. The diphenylsilane diol was dissolved in pyridine and one-half of the toluene was placed in an agitated vessel which was chilled. The chlorosilanes were then dissolved in the remainder of the toluene and were placed in the addition vessel. The silanes were then added to the pyridine silane diol mixture at a rate which would allow the cooling system to keep the reaction mixture at 5° to 7° C. Careful control was now required but for maximum yield the temperature did not exceed 10° C. In the laboratory, the addition required 3 to 4 hours for about a 5-liter batch. After all the silanes had been added, the vessel was agitated for one hour and allowed to cool to room temperature. The pyridine salts were filtered and the solution was removed to a constricting vessel. The pyridine hydrochloride was then dissolved in equal weight of water and the residual solution was separated with soda ash (2%) and added to a constricting vessel. The solution was then stripped of toluene, pyridine hydrochloride which was stripped out at 20 mm pressure and about 150° C. temperature. The separation procedure and distillation procedure of the desired product was as in Example 3 above. As a result of the procedure there was obtained the following products:

| | Boiling Point |
|---|---|
| $(CH_3)_2\phi Si-O-\underset{\underset{\phi}{\vert}}{\overset{\overset{\phi}{\vert}}{Si}}-O-Si(CH_3)_2\phi$ | 200 mm - 183° C. |
| $(CH_3)_2\phi Si-O-\underset{\underset{\phi}{\vert}}{\overset{\overset{\phi}{\vert}}{Si}}-O-Si\phi_2CH_3$ | 200 mm - 226° C. |
| $\phi_2CH_3Si-O-\underset{\underset{\phi}{\vert}}{\overset{\overset{\phi}{\vert}}{Si}}-O-Si\phi_2CH_3$ | 200 mm - 260° C. |

The yield of the desired product was 45% weight with a possible theoretical yield of 80% by following an equilibration procedure.

EXAMPLE 5

The following four compounds were tested in the G-4 test for vacuum efficiency:

| Symbol | Formula |
|---|---|
| X | Mixture of T cyclics |
| 2X | (CH₃)₃SiO—Si(O—)(φ)—O—Si(φ)—O—Si(CH₃)₃ with (CH₃)₃Si— group |
| 3X | (CH₃)₃SiO—SiO(φ)—Si(O—)(φ)—Si(φ)—OSi(CH₃)₃ with two (CH₃)₃Si— groups |
| 4X | (CH₃)₃Si—O—Si(φ)—O—Si(φ)(O—)—Si(φ)—OSi(CH₃)₃ with (CH₃)₃Si— group |

The results of the test are presented in the Table I below:

TABLE I

| | | Vacuum in G-4 Test | | |
|---|---|---|---|---|
| Compound | Boiling Range | 1 Hour | 2 Hours | 4 Hours |
| 4X | 244–265° C. | $6 \times 10^{-6}$ | $2 \times 10^{-6}$ | $1.5 \times 10^{-6}$ |
| 3X | 245° C. | $2 \times 10^{-6}$ | $1 \times 10^{-6}$ | $1 \times 10^{-6}$ |
| 2X | 185–195° C. | $6 \times 10^{-5}$ | $2 \times 10^{-5}$ | $8.1 \times 10^{-6}$ |
| X | 175–185° C. | $2 \times 10^{-4}$ | | |

I claim:

1. A process for forming inexpensive silicone diffusion pump fluids capable of maintaining a vacuum of $1 \times 10^{-6}$ in a vacuum pump comprising (1) reacting sufficient amounts of an aliphatic alcohol having 1 to 3 carbon atoms with phenyltrichlorosilane so as to substitute on the average from 30% to 80% of the chlorine groups in said silane with alkoxy groups so as to produce an alkoxylated phenylchlorosilane at a temperature of −8 to 25° C.; (2) adding at least the stoichiometric amount of water to the mixture of said alkoxylated phenylchlorosilane, trimethylchlorosilane and a phenyl compound selected from the class consisting of diphenyldichlorosilane and diphenylsilane diol to form a mixture of diffusion pump fluids which are phenylsiloxane fluids, and (3) separating all the different fluids by fractional distillation.

2. A process for forming inexpensive silicone diffusion pump fluids capable of maintaining a vacuum of $1 \times 10^{-6}$ mm Hg pressure at 25° C. in a vacuum pump comprising;
(1) reacting sufficient amounts of ethanol with phenyltrichlorosilane so as to substitute on the average from 60% to 70% of the chlorine groups in said silane with alkoxy groups so as to produce an alkoxylated phenylchlorosilane at a temperature of −8 to 25° C.;
(2) adding at least the stoichiometric amount of water to the mixture of said alkoxylated phenylchlorosilane, trimethylchlorosilane and a phenyl compound selected from the class consisting of diphenyldichlorosilane and diphenylsilane diol to form a mixture of diffusion pump fluids which are phenylsiloxane fluids, and
(3) separating all the different fluids by fractional distillation.

3. The process of claim 2 wherein in step (1) at least 2 moles of ethanol are reacted with one mole of phenyltrichlorosilane.

4. The process of claim 3 wherein in step (1) after the formation of the alkoxylated phenylchlorosilane the excess alcohol and HCl that is formed is stripped off by heating the mixture at a temperature of 25° to 50° C.

5. The process of claim 2 wherein in step (2) there is reacted at least 2 moles of the alkoxylated phenylchlorosilane with at least 4 moles of the trimethylchlorosilane with 1 mole of the phenyl compound which is diphenyldichlorosilane.

6. The process of claim 5, wherein in step (2) there is added at least 10% in excess over the stoichiometric amount of water necessary to hydrolyze all the chlorine groups and alkoxy groups in the reactants.

7. The process of claim 5 wherein step (2) is carried out at a temperature in the range of 5° to −8° C.

8. The process of claim 7 wherein the water is added to the mixture of chlorosilanes continuously and incrementally over a 2 to 4 hour period of time.

9. The process of claim 8 wherein in step (2) the reaction period of time varies from 2 to 6 hours.

10. The process of claim 9 wherein after step (2) is completed the phenyl siloxane fluid products are washed with water until they contain less than 15 parts per million of acid and are also neutralized with a mild base if necessary.

11. The process of claim 10 wherein the mild base is sodium bicarbonate.

12. The process of claim 2 wherein in step (1) at least one mole of methanol is reacted with one mole of phenyltrichlorosilane.

* * * * *